US012778385B2

(12) United States Patent
Weis

(10) Patent No.: US 12,778,385 B2
(45) Date of Patent: Nov. 3, 2026

(54) METHOD AND SYSTEM FOR SELF-CHECKING OF AN ENDOSCOPE REPROCESSING DEVICE

(71) Applicant: OLYMPUS Winter & Ibe GmbH, Hamburg (DE)

(72) Inventor: Antonia Weis, Hamburg (DE)

(73) Assignee: OLYMPUS Winter & Ibe GmbH, Hamburg (DE)

(*) Notice: Subject to any disclaimer, the term of this patent is extended or adjusted under 35 U.S.C. 154(b) by 281 days.

(21) Appl. No.: 18/371,190

(22) Filed: Sep. 21, 2023

(65) Prior Publication Data

US 2024/0172921 A1 May 30, 2024

Related U.S. Application Data

(60) Provisional application No. 63/428,493, filed on Nov. 29, 2022.

(51) Int. Cl.
*A61B 1/00* (2006.01)
*A61B 1/015* (2006.01)
*A61B 1/12* (2006.01)

(52) U.S. Cl.
CPC .......... *A61B 1/00057* (2013.01); *A61B 1/015* (2013.01); *A61B 1/125* (2013.01); *A61B 1/12* (2013.01); *A61B 1/123* (2013.01)

(58) Field of Classification Search
CPC . A61B 1/00057; A61B 1/015; A61B 1/00–32; A61B 1/121; A61B 1/123;
(Continued)

(56) References Cited

U.S. PATENT DOCUMENTS

2004/0091389 A1* 5/2004 Malkin .................. A61B 1/123 422/26
2007/0169799 A1 7/2007 Noguchi et al.
(Continued)

FOREIGN PATENT DOCUMENTS

JP 2011521751 A 7/2011

OTHER PUBLICATIONS

Translation of Japanese Office Action dated Jan. 13, 2026 received in 2023-199289.

*Primary Examiner* — Anhtuan T Nguyen
*Assistant Examiner* — James Edward Boice
(74) *Attorney, Agent, or Firm* — Scully, Scott, Murphy & Presser, P.C.

(57) ABSTRACT

A method for self-checking of an endoscope reprocessing device having a fluid source, supply channels for supplying the fluid to endoscope channels of an endoscope(s) connected with the supply channels, and a controller for controlling the reprocessing of endoscope(s). Each of the supply channels having a switchable valve configured to block or unblock the supply channel in response to a control signal. The method including: reprocessing the endoscope(s); carrying out a running self-check of the reprocessing device comprising keeping a history of flow test results, updating the history with latest flow test results and carrying out an analysis of the history of flow test results for each of the supply channels; and indicating a problem with one or more supply channels or a valve associated therewith if the history of flow test results contains one or more flow test result anomalies that meet at least one or more predefined criteria.

16 Claims, 2 Drawing Sheets

(58) Field of Classification Search
CPC ... A61B 1/12–125; B08B 9/0321; B08B 9/02; B08B 9/027; B08B 13/00; B08B 2209/027; B08B 2209/032
USPC .............. 600/118, 155; 604/264; 134/166 R, 134/168 C
See application file for complete search history.

(56) References Cited

U.S. PATENT DOCUMENTS

| | | | | |
|---|---|---|---|---|
| 2011/0126868 | A1 | 6/2011 | Waldmann et al. | |
| 2013/0098400 | A1* | 4/2013 | Nguyen | B08B 9/00 134/18 |
| 2015/0161678 | A1* | 6/2015 | Dasdan | G06F 8/4441 705/14.71 |
| 2015/0374868 | A1* | 12/2015 | Bruce | A61L 2/24 422/119 |
| 2017/0172399 | A1* | 6/2017 | Takada | A61B 1/00057 |
| 2018/0028051 | A1* | 2/2018 | Boettcher-Wilmes | A61B 1/121 |
| 2019/0076009 | A1* | 3/2019 | Yang | A61B 90/70 |
| 2021/0298871 | A1* | 9/2021 | Nishiyama | A61B 1/00057 |
| 2022/0216688 | A1* | 7/2022 | Han | H02H 3/325 |

* cited by examiner

METHOD AND SYSTEM FOR SELF-CHECKING OF AN ENDOSCOPE REPROCESSING DEVICE

CROSS-REFERENCE TO RELATED APPLICATION

The present application is based upon and claims the benefit of priority from U.S. Provisional Patent Application No. 63/428,493, filed on Nov. 29, 2022, the entire contents of which is incorporated herein by reference.

BACKGROUND

Field

The present disclosure refers to a method and a system for self-checking of an endoscope reprocessing device having a source for reprocessing fluid, a source for pressurized air, a plurality of supply channels for supplying reprocessing fluid and/or pressurized air from the sources to individual channels of endoscopes connected with the supply channels of the reprocessing device for reprocessing, and a controller for controlling the reprocessing of endoscopes, each supply channel having a dedicated switchable valve for alternatively blocking and opening the supply channel in response to control signals issued by the controller.

Prior Art

Endoscope reprocessing devices such as the applicant's ETD series devices generally have a washing cabinet with, e.g., baskets for receiving endoscopes to be reprocessed and adapters with which to connect endoscope channels to supply channels of the endoscope reprocessing device. During reprocessing, the endoscope reprocessing device circulates reprocessing fluid through the various endoscope channels and after completion switches over to drying air which is supplied out of a pressurized air source.

A flow control unit of the endoscope reprocessing device is situated at the interface between the water and pressurized air supplies and the washing cabinet. The flow control receives the reprocessing fluid and pressurized air from the respective source and distributes it into one or a plurality of dedicated supply channels that each are equipped with an electronically controllable valve for individually reprocessing the different endoscope channels.

The endoscope reprocessing device, and in particular the flow control unit, is equipped with diagnostic equipment, in particular pressure sensors that are connected to the one or more individual supply channels downstream of the respective valve as well as one or more pressure sensors connected to the common channel from which the supply channels branch off. This sensor suite measures the pressure as supplied by the pressurized air source as well as the pressures inside the supply channels, which reflect the pressure inside the individual endoscope channels. These measurements are used for flow tests through the individual endoscope channels prior to, during and/or after reprocessing that can reveal blockages, obstructions or leakages of individual endoscope channels.

Such flow tests are usually done for each endoscope channel individually, one at a time. They may involve two stages, the first being opening the valve of the supply channel to which the endoscope channel to be tested is connected, feeding pressurized air into the endoscope channel. After a brief period of the system reaching an equilibrium, the difference is measured between the pressure of the pressurized air provided by the pressurized air source and as measured in the common channel of the flow control unit and the pressure in the supply channel measured with the pressure sensor connected to the supply channel downstream of the respective valve. If this first pressure difference lies between a pre-set maximum pressure difference and a pre-set minimum pressure difference, the first stage of the flow test is completed successfully. The pre-set maximum and minimum pressure differences may vary for different types of endoscopes, and per endoscope channel, e.g., depending on its diameter.

For the second stage of the flow test, the valve in the supply channel is closed. This results in the pressure in the endoscope channel, as measured by the pressure sensor downstream of the now closed valve, drops off with a rate typical for the respective type of endoscope and/or endoscope channel. In this second stage, the difference in pressure between the supply channel pressure as measured in the first stage and the progression of the decreasing supply channel pressure is measured and again analyzed with respect to lying within an allowed range between a minimum and a maximum pressure difference, which may again be pre-set according to endoscope type specifications.

Irregular flow test results, i.e., results that are not in line with specifications, in the first and/or second stage of the flow test, will be reported such that an endoscope may be sent for further cleaning, repair or discarding, as the case may be.

The reprocessing and flow test analysis rely on all components of the endoscope reprocessing device being in working order and being calibrated within specifications. To ensure the continuing serviceability of the endoscope reprocessing device, it is prompted to perform self-checks in regular service intervals, at which occasion the calibration of the pressure sensors is checked and, if necessary, updated. These self-checks are performed using standardized test plates that are inserted into the washing cabinet and connected to the supply channels leading out of the flow control unit. The test plates have orifices of well-known dimensions in order to provide a standardized environment for reproducible flow test results without the uncertainty of real endoscope channels that might deviate from their design specifications. Following a self-check, the endoscope reprocessing device may have to be serviced or repaired, until its functioning according to design specifications is restored.

In the daily routine of reprocessing of endoscopes, irregular flow test results therefore usually indicate problems with the endoscope being reprocessed and tested. However, in some cases, a problem may also have occurred in the endoscope reprocessing device, in particular in one or more of its supply channels. Also, there may be a problem with an adapter that might not have been properly connected to its designated endoscope channel and might have fallen off or failed to properly seal with it.

In both cases, the flow test results will show irregularities. Since the endoscope reprocessing device is assumed to function properly, these irregularities will then be attributed to a problem with the respective endoscope channel. This erroneous attribution of the cause of the problem leads to a false negative result for this specific endoscope channel that in reality does not have a problem. The problem residing in the reprocessing device, on the other, remains undetected.

SUMMARY

An object is to provide a system and method that alleviate the aforedescribed drawbacks of the known endoscope reprocessing devices.

Such object can be solved by a method for self-checking of an endoscope reprocessing device having at least one source for a fluid, such as a source for a reprocessing fluid and/or a source for pressurized air, one or more supply channels for supplying a fluid from the at least one source to one or more individual channels of one or more endoscopes connected with the one or more supply channels of the reprocessing device for reprocessing, and a controller for controlling the reprocessing of endoscopes, each of the one or more supply channel having a dedicated switchable valve configured to let through the fluid and to block the supply channel in response to control signals issued by the controller, the method comprising reprocessing of one or more endoscopes that are connected to the reprocessing device for reprocessing, the reprocessing of the one or more endoscopes comprising a flow test during which pressures or pressure differences are checked in a sequence of application and blocking of the fluid in the one or more channels of the one or more endoscopes connected to the reprocessing device for identification of anomalies occurring at the one or more individual endoscope channels, wherein a running self-check of the reprocessing device is carried out, the running self-check comprising keeping a history of flow test results, updating the history with the latest flow test results and carrying out an analysis of the history of flow test results for each of the one or more supply channels of the reprocessing device, wherein a problem with a supply channel or a valve associated with the supply channel is indicated if the history of flow test results contains flow test result anomalies in the supply channel that meet at least one or more predefined criteria.

This method can provide functionality for self-checking of endoscope reprocessing devices that does not rely on dedicated self-checks, but can be carried out in the course of normal endoscope reprocessing operations. The method does not require any additional hardware. It can be implemented as an update to the control or diagnostics software and runs on at least one of the main controller of the reprocessing device, within the flow controller of the reprocessing device or an external computer system (see computer system 105 at FIG. 1 that is connected with the reprocessing device via wired or wireless datalink, represented at 115, for example internet or intranet).

The underlying measurements of fluidic pressure can be the measurement of a reprocessing fluid pressure or of a pressure of pressurized air, or both, as the case may be.

The feature of keeping a history of flow test results, updating the history with the latest flow test results and carrying out an analysis of the history of flow test results makes it possible to analyze the history of flow test results for irregularities that can be traced back to problems with the reprocessing device itself, such as the supply channel or channels thereof. Since the method can identify problems of the reprocessing device, it can provide a self-check functionality for the reprocessing device. Since this analysis can be done in the context of every single endoscope reprocessing operation, this self-check functionality can comprise a running self-check for the reprocessing device. The running self-check complements the dedicated self-checks that are carried out during routine servicing of the reprocessing device.

The running self-check can be done for the one or more individual supply channels of the endoscope reprocessing device. Problems can occur and be identified in one, several or all of the supply channels.

The keeping and updating of the history of flow test results may be realized by keeping a history of individual flow tests including all the measurement data taken during the flow tests and the flow test result, or, in an abbreviated form, including only test results, such as error flags raised during test results, or simply a running count of errors.

In an embodiment of the method, a flow test result anomaly can be a blockage of an endoscope channel connected with the supply channel or a problem with the attachment of an endoscope channel to the supply channel. The blockage of the channel may indicate a problem with the supply channel since, in the case of a single measurement, it may not be possible to distinguish between a real blockage of the endoscope channel, a sensor malfunction and a malfunction of the valve. The same holds true for cases, where the endoscope channel has disconnected itself from the supply channel, for example fallen off.

In embodiments, the one or more predefined criteria can be met for the supply channel when flow test result anomalies identified during flow testing of endoscope channels connected with the supply channel have occurred at least a first predefined number $N_1$ of times within a second predefined number $N_2$ of the most recent flow tests, with $N_2$ being greater than $N_1$. This criterion is based on the fact, that flow test results anomalies usually have a certain low probability of occurring. This probability may be known from experience or from prior testing of such scenarios. The predefined numbers $N_1$ and $N_2$ may be chosen such that they indicate a statistically significant clustered occurrence of flow test result anomalies. For example, $N_2$ may be chosen such that the problem occurring in the reprocessing device is caught shortly after its first occurrence in order to facilitate a quick response and remedy to the problem with the reprocessing device, for example by scheduling an out-of-turn maintenance or repair.

In embodiments, the one or more predefined criteria can be met for the supply channel when flow test result anomalies identified during flow testing of endoscope channels connected with the supply channel have occurred a third predefined number of times $N_3$ in succession. This criterion is stricter than the previously described criteria, since it requires flow test results anomalies in the same supply channel in uninterrupted succession. Since usually reprocessing operations are done with different endoscopes, it is highly unlikely that flow test result anomalies occur at the same supply channel several times in a row, so that a sufficient statistical significance is reached very quickly. The number of times $N_3$ may therefore be chosen smaller than $N_2$, the latter of which allows for only sporadic occurrences of flow test results anomalies.

In the case of successive flow test results anomalies associated with a single supply channel, a counter counting the number of times in which flow test result anomalies have been identified in successive flow tests of endoscope channels connected with the supply channel may be reset when a new flow test of an endoscope channel connected with the supply channel does not turn up a flow test result anomaly. Such counters may be defined for each of the supply channels.

In embodiments of the method, counters for the number of identifications of test flow anomalies can be reset after a dedicated self-check of the reprocessing device, such as using a test plate connected to the supply channels.

In embodiments of the method, the flow tests of endoscope channels connected with one or more of the supply channels are performed sequentially one after another at least one of before, during and after reprocessing of an endoscope.

In further embodiments, a message reporting a finding can be generated and displayed or transmitted to a user or to a service provider in the event that a problem with a particular supply channel or valve associated with the supply channel is identified.

Such object can also be solved by an endoscope reprocessing device comprising a washing cabinet configured for receiving one or more endoscopes to be reprocessed, a main controller configured for controlling the reprocessing of endoscopes, at least one source for a fluid controlled by the main controller, such as a source for reprocessing fluid and/or a source for pressurized air, and one or more supply channels connected to the at least one source for fluid leading to the washing cabinet, each of the one or more supply channels having an electronically controlled valve for opening and closing the respective supply channel and a pressure sensor connected to the supply channel downstream of the valve, wherein the device is configured for carrying out a running self-check of the reprocessing device, the running self-check comprising keeping a history of flow test results, updating the history with the latest flow test results and carrying out an analysis of the history of flow test results for each of the one or more supply channels of the reprocessing device, wherein a problem with a supply channel of the one or more supply channels or a valve associated with the supply channel is indicated if the history of flow test results contains flow test result anomalies in the supply channel that meet at least one or more predefined criteria.

The endoscope reprocessing device embodies the same advantages, features and characteristics as the above described method.

In embodiments, the at least one source for fluid, such as the sources for reprocessing fluid and for pressurized air, is or are connected via a switchable valve to a common bus channel from which the supply channels branch off, wherein the switchable valve can have two positions for alternatively letting through reprocessing fluid and pressurized air, and can also include a third position for closing off both reprocessing fluid and pressurized air.

In alternative embodiments, the sources for reprocessing fluid and for pressurized air can be connected directly to the one or more supply channels, wherein the switchable valves can have three positions, a first position for letting through processing fluid, a second position for letting through pressurized air and a third position for closing off the supply channel.

In some embodiments, a flow controller in communication with the main controller is configured to control the operation of the electronically controlled valves of the one or more supply channels.

In embodiments, at least one of the main controller and the flow controller is or are configured for carrying out embodiments of the above-described method.

BRIEF DESCRIPTION OF THE DRAWINGS

Further characteristics will become apparent from the description of the embodiments together with the claims and the included drawings. Embodiments can fulfill individual characteristics or a combination of several characteristics.

The embodiments are described below, without restricting the general intent of the invention, based on exemplary embodiments, wherein reference is made expressly to the drawings with regard to the disclosure of all details that are not explained in greater detail in the text. In the drawings.

In the drawings, the same or similar types of elements or respectively corresponding parts are provided with the same reference numbers in order to prevent the item from needing to be reintroduced.

DETAILED DESCRIPTION

Figure 1:
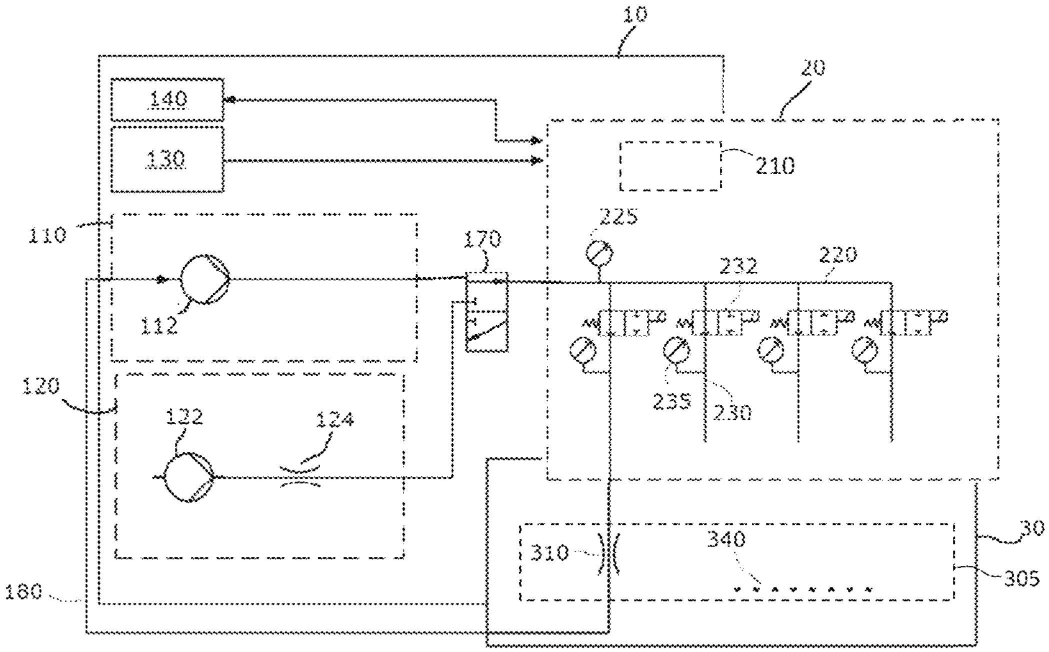
FIG. 1 illustrates a schematic representation of an endoscope reprocessing device.

FIG. 1 shows a schematic representation of an endoscope reprocessing device 10, which includes a flow control unit 20 and a washing cabinet 30. The flow control unit 20 may be an integral part of the reprocessing device 10, the latter having the sole controller in the form of main controller 140, or it may have its own flow controller 210 in communication with the main controller 140. The controllers can be implemented by hardware, such as circuits, processor, CPU etc. or any combination of hardware and software stored in an associated memory. The endoscope reprocessing device 10 features a reprocessing fluid supply 110 and a pressurized air supply 120, which supply a reprocessing fluid and pressurized drying air, respectively, to endoscopes (not shown) that have been put into washing baskets inside the washing cabinet 30 and connected to adapters that are ultimately connected to the reprocessing fluid supply 110 and the pressurized air supply 120.

The reprocessing fluid supply 110 has a pump 112, e.g., a circulation pump, receiving reprocessing fluid back from the washing cabinet 30 by way of a return duct 180. Pump 112 may pump the reprocessing fluid through other parts, such as a filter or a secondary pump tasked with providing the required flow rate and pressure of the reprocessing fluid to the endoscopes to be reprocessed.

The pressurized air supply 120 may have a pump as a pressurized air source 122, which supplies pressurized air for drying and for conducting flow tests to the endoscopes. The regulation of the flow rate and pressure of the pressurized air flow into the endoscopes may be aided by an adjustment valve 124.

Such self-checks can be performed using standardized test plates 305 that are inserted into the washing cabinet and connected to the supply channels leading out of the flow control unit. The test plates 305 have orifices of well-known dimensions in order to provide a standardized environment for reproducible flow test results without the uncertainty of real endoscope channels that might deviate from their design specifications.

An electronically controlled switchable valve 170 that may be actuated pneumatically, hydraulically or electrically is used to switch back and forth between supply of processing fluid and pressurized air. The control of the valve 170 as well as other controllable parts of the endoscope reprocessing device 10 and the flow control unit 20 is carried out by the main controller 140 having control over reprocessing operation as well as other functionality, such as self-checking of the device.

Another component of the endoscope reprocessing device 10 is a power supply 130. An endoscope type list having reprocessing and testing parameters for all the types of endoscopes that the endoscope reprocessing device 10 is cleared to reprocess may be stored in a memory of the main controller 140.

The flow control unit 20 has a common channel 220 connected to the outlet of switching valve 170 and thus alternately receives reprocessing fluid and pressurized air from their respective supplies, depending on the switch status of valve 170. A pressure sensor 225 is connected to the common channel 220, providing sensor readings for the fluid or air pressure inside the common channel 220 as supplied by the fluid and air supplies 110 and 120. The common channel 220 branches off into a plurality of supply channels 230 that lead to an adapter or adapters at the interface to the washing cabinet 30, to which the channels of an endoscope to be reprocessed will be connected. FIG. 1 shows a device having four supply channels 230, only one of which is provided with reference numbers for clarity's sake. The other supply channels are outfitted in similar fashion and may vary in diameter or other parameters depending on the type of endoscope channels for which they are usually used, but usually not in overall functionality. In place of the four supply channels depicted here, fewer or more supply channels may be used, as the case may be. In the case of an elevator channel with an APC (Albarrán Pressure Control), there may be only one supply channel present, with in some cases more supply channels in a parallel unit.

In the embodiment depicted in FIG. 1, all of the supply channels 230 each have an electronically controllable switchable valve 232 for opening or closing off the respective supply channel 230, as well as a pressure sensor 235 connected to the respective supply channel 230 downstream of the respective valve 232. In this way, it is possible to measure the pressure present in each supply channel 230 individually both when the valve 232 is open or closed, respectively, and independently of the pressure inside the common channel 220.

The flow control unit 20 may have the dedicated flow controller 210 locally controlling operations of components of the flow control unit 20. The dedicated mainboard may be in data communication with the main controller 140 and receive commands to be carried out by the flow control unit 20.

For each of the supply channels 230 of the flow control unit 20, the washing cabinet 30 has a coupling to an endoscope channel comprising a constriction to the flow of reprocessing fluid and pressurized air. A further constriction 310 represents, e.g., an adapter and an endoscope connected to the supply channel 230. Further identical sorts of couplings 340 are symbolized as " . . . " in FIG. 1.

In alternative versions of the reprocessing device, the flow control unit 20 may be equipped with its own controller in communication with main controller 130. Furthermore, either switchable valve 170 or switchable valves 232 may be connected directly to the fluid and air supplies 110, 120 and have three positions, namely open for pressurized air, open for reprocessing fluid and closed. In the latter case, there may be two common channels 220, one for pressurized air and one for the reprocessing fluid.

The reprocessing device 10 including the flow control unit 20 and the washing cabinet 30 is equipped to reprocess endoscopes, conduct flow tests and a running self-check.

Figure 2:
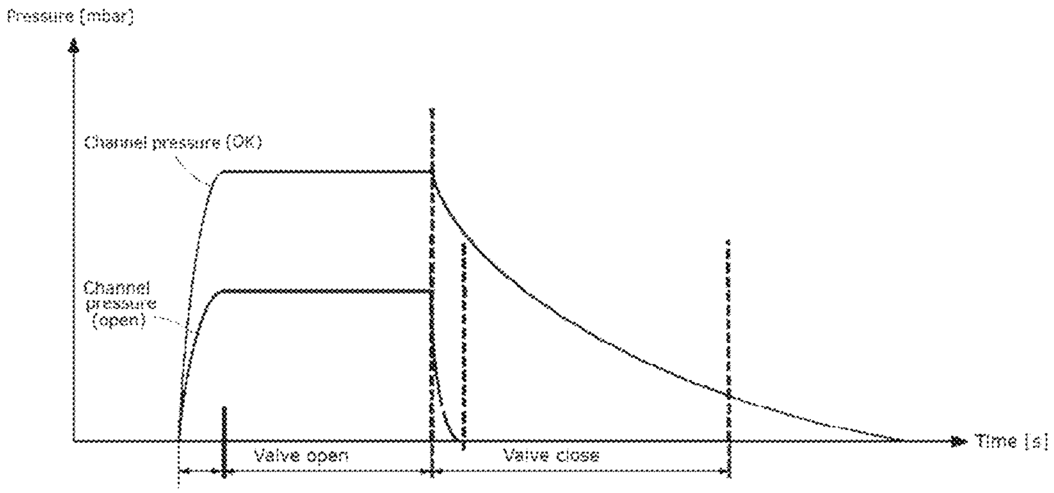
FIG. 2 illustrates an annotated representation of flow test curves.

FIG. 2 shows an annotated representation of flow test curves, pressure and time being the vertical and horizontal axes of the graph, respectively. The fluid pressure during a flow test of an endoscope channel connected to a single supply channel 230 is depicted over time for two scenarios. The fluid may be a reprocessing fluid or pressurized air, for example.

A typical flow test of an endoscope channel may have two stages. The first stage involves opening the valve 232 of a supply channel 230, allowing the fluid to run through an endoscope channel connected to the supply channel 230. There is a brief period of build-up of fluid pressure as the valve 232 opens until an equilibrium is reached. After a predetermined time, the second stage is started by closing the valve 232 again. The drop off of the supply channel pressure is then measured for a certain time.

A simple case (not shown) is present if an endoscope channel is fully blocked. In that case, the fluid pressure will go up quickly and stay at a high level, at or slightly under the pressure the pressurized fluid is supplied with. In that case, the pressurized fluid cannot escape through the blocked endoscope channel and remains high throughout the flow test. In this case, a "channel blocked" flag or some other indication of the blockage will be recorded and displayed. This case is not shown in FIG. 2.

At the other extreme, the supply channel 230 may be open, for example because of a connection failure, possibly with the adapter having fallen off. This is presented by the curve annotated with "Channel pressure (open)". In that case, after the application of pressurized fluid by opening the valve 232 of the supply channel 230, the pressure as measured rises to a constant, but low value. When valve 232 is closed, the pressure drops off very fast since the pressurized fluid escapes rapidly and unrestrictedly from the open end of the supply channel 230. This curve is typical for the condition "not connected", which may also be recorded and displayed.

The second case displayed in FIG. 2 is one in which no fault is found. In the curve annotated with "Channel pressure (OK)", the pressurized air has to make its way through the endoscope channel that is attached to the supply channel, which constitutes a further restriction to the flow of pressurized fluid. For this reason, the pressure in the supply channel 230 rises quickly to a constant equilibrium value within boundaries that may be preset according to pre-known endoscope type specifications, either as absolute values or as pressure differences towards the supplied fluid pressure. The equilibrium pressure, as well as the boundary values, are furthermore lower than the pressure in case of a blocked channel and higher than the pressure observed when the end of the supply channel 230 is not connected.

Likewise, after closing valve 232, the pressurized fluid has to escape through the endoscope channel, and therefore much more slowly than in the case of the unconnected, i.e., open ended supply channel 230. The curve showing the decreasing pressure in the supply channel 230 runs through a window (not shown) of allowed values between a maximum and a minimum pressure or pressure difference, e.g., between the measured supply channel pressure before the valve 232 was opened and the presently measured decreasing supply channel pressure. If, at a predetermined time or at predetermined times after closing valve 232, the measured supply channel pressure lies within these boundaries, the endoscope channel will have passed the second stage of the flow test.

Figure 3:
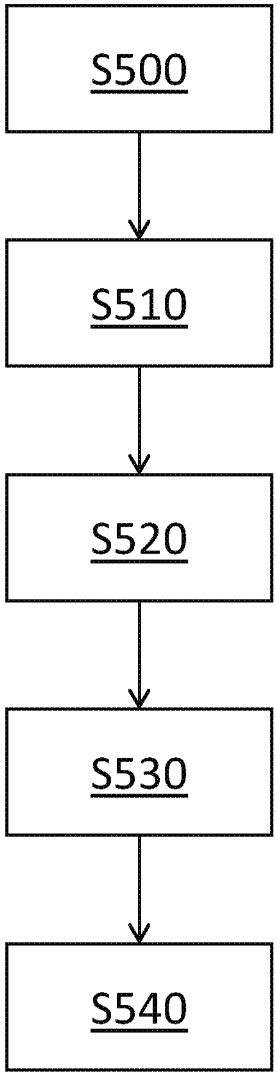
FIG. 3 illustrates a flow diagram of a running self-check.

FIG. 3 is a flow diagram of an iteration of a running self-check. In step S500, an endoscope is reprocessed in the endoscope reprocessing device 10. Before, during and/or after the reprocessing itself, the endoscope channels are subjected to a flow test in step S510, as described in the context of FIG. 2. The endoscope may pass the flow test, or an irregularity may be found, such as a blocked channel or an adapter having fallen off.

The results of the flow test of the present reprocessing operation are then used to update a flow test result history in step S520. A minimum content of the update to the flow test result history is the result of the flow test for each channel, but may also include a time stamp, information about the type of endoscope tested or other information that may be deemed relevant for subsequent analysis.

In step S530 the flow test result history, having been updated with the most recent results, is analyzed for anomalies, such as a statistically significant clustering of anomalous or irregular test results in one or several of the channels, or the occurrence of several consecutive irregular test results in one of the channels. If such a clustering or consecutive occurrence is found, the problem may be reported in step S540, in order to alert a user that the endoscope reprocessing device is in need of servicing or repair.

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCES

10 reprocessing device
20 flow control unit
30 washing cabinet
105 computer system
110 reprocessing fluid supply
112 pump
115 datalink
120 pressurized air supply unit
122 pressurized air source
124 adjustment valve
130 power supply
140 main controller
170 switchable valve
180 return duct
220 common channel
210 flow controller
225 pressure sensor
230 supply channel
232 switchable valve
235 pressure sensor
305 test plate
310 constriction
340 further couplings
S500 reprocessing of endoscope
S510 flow test
S520 update history of flow test results
S530 analyze history of flow test results
S540 identify/report problem

What is claimed is:

1. A method for self-checking of an endoscope reprocessing device having at least one source for a fluid, one or more supply channels for supplying the fluid from the at least one source to one or more individual endoscope channels of one or more endoscopes connected with the one or more supply channels, and a controller for controlling the reprocessing of endoscopes, each of the one or more supply channels having a dedicated switchable valve configured to let through the fluid and to block the supply channel in response to a control signal issued by the controller, the method comprising:

reprocessing the one or more endoscopes connected to the reprocessing device, the reprocessing of the one or more endoscopes comprising a flow test during which one of pressures or pressure differences are checked in a sequence of application and blocking of the fluid in the one or more endoscope channels connected to the reprocessing device for identification of anomalies occurring at the one or more individual endoscope channels;

carrying out a running self-check of the reprocessing device, the running self-check comprising keeping a history of flow test results from a plurality of prior reprocessing operations, and at every reprocessing operation, when the flow test results are available for the latest reprocessing operation, updating the history with latest flow test results from the plurality of prior reprocessing operations with the latest flow test results and carrying out an analysis of the updated history of flow test results for each of the one or more supply channels of the reprocessing device to evaluate whether the history satisfies one or more predefined criteria; and indicating a problem with one of a supply channel of the one or more supply channels or a valve associated with the supply channel if the updated history of flow test results contains one or more flow test result anomalies in the supply channel that meet at least one or more predefined criteria.

2. The method according to claim 1, wherein the one or more flow test result anomalies is a blockage of an endoscope channel connected with the supply channel or a problem with the attachment of an endoscope channel to the supply channel.

3. The method according to claim 1, wherein the one or more predefined criteria is met for the supply channel when the one or more flow test result anomalies identified during flow testing of endoscope channels connected with the supply channel have occurred at least a first predefined number $N_1$ of times within a second predefined number $N_2$ of the most recent flow tests, with $N_2$ being greater than $N_1$.

4. The method according to claim 3, wherein the one or more predefined criteria is met for the supply channel when flow test result anomalies identified during flow testing of endoscope channels connected with the supply channel have occurred a third predefined number of times $N_3$ in succession.

5. The method according to claim 4, further comprising resetting a counter counting the number of times in which the one or more flow test result anomalies have been identified in successive flow tests of endoscope channels connected with the supply channel when a new flow test of an endoscope channel connected with the supply channel does not turn up a flow test result anomaly.

6. The method according to claim 1, further comprising resetting counters for the number of identifications of the one or more test flow anomalies after a dedicated self-check of the reprocessing device.

7. The method according to claim 6, wherein dedicated self-check comprises using a test plate connected to the one or more supply channels.

8. The method according to claim 1, wherein the flow tests of endoscope channels connected with the one or more supply channels are performed sequentially one after another or in several or all of the one or more supply channels in parallel at least one of before, during and after reprocessing of an endoscope.

9. The method according to claim 1, further comprising generating and displaying or transmitting a message reporting a finding to a user or to a service provider in the event that a problem with the supply channel or valve associated with the supply channel is identified.

10. An endoscope reprocessing device comprising:

a washing cabinet configured to receive one or more endoscopes to be reprocessed;

a controller;

at least one source for a fluid controlled by the controller; and one or more supply channels connecting the at least one source for fluid to the washing cabinet, each of the one or more supply channels having an electronically controlled valve for opening and closing a respective supply channel and each of the one or more supply channels having a pressure sensor connected to the respective supply channel downstream of the valve;

wherein the controller is configured to:

carry out a running self-check of the reprocessing device, the running self-check comprising keeping a history of flow test results from a plurality of prior reprocessing operations, and at every reprocessing operation, when the flow test results are available for the latest reprocessing operation, updating the history with latest flow test results from the plurality of prior reprocessing operations with the latest flow test results and carrying out an analysis of the updated history of flow test results for each of the one or more supply channels to evaluate whether the history satisfies one or more predefined criteria, and indicating a problem with a supply channel of the one or more supply channels or a valve associated with the supply channel if the updated history of flow test results contains one or more flow test result anomalies in the supply channel that meet at least one or more predefined criteria.

11. The endoscope reprocessing device according to claim 10, wherein the at least one source for fluid is connected via a switchable valve to a common bus channel from which the one or more supply channels branch off.

12. The endoscope reprocessing device according to claim 11, wherein the at least one source for fluid comprises a reprocessing fluid supply and pressurized air supply, the switchable valve has two positions for alternatively letting through the reprocessing fluid and the pressurized air.

13. The endoscope reprocessing device according to claim 12, wherein the switchable valve has a third position for closing off both the reprocessing fluid and the pressurized air.

14. The endoscope reprocessing device according to claim 11, wherein the at least one source for fluid comprises a reprocessing fluid supply and pressurized air supply and the reprocessing fluid supply and the pressurized air supply are connected directly to the one or more supply channels, wherein the switchable valve has three positions, a first position for letting through the processing fluid, a second position for letting through the pressurized air and a third position for closing off the supply channel.

15. The endoscope reprocessing device according to claim 10, further comprising a flow control unit in communication with the controller, the flow control unit having a flow controller being configured to control an operation of the electronically controlled valves of the one or more supply channels.

16. The endoscope reprocessing device according to claim 10, wherein the controller is one of a main controller configured to control the reprocessing of endoscopes, a flow controller being configured to control an operation of the electronically controlled valves of the one or more supply channels or a computer system connected via a datalink to the endoscope reprocessing device.

* * * * *